United States Patent
Gartside et al.

(10) Patent No.: US 8,314,280 B2
(45) Date of Patent: Nov. 20, 2012

(54) PROCESS FOR THE PRODUCTION OF OLEFINS

(75) Inventors: Robert J. Gartside, Summit, NJ (US); Robert Haines, Kinnelon, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 381 days.

(21) Appl. No.: 12/720,975

(22) Filed: Mar. 10, 2010

(65) Prior Publication Data

US 2010/0240937 A1 Sep. 23, 2010

Related U.S. Application Data

(60) Provisional application No. 61/162,074, filed on Mar. 20, 2009.

(51) Int. Cl.
*C07C 4/06* (2006.01)

(52) U.S. Cl. ........ 585/648; 585/653; 585/649; 585/650; 585/906; 585/910

(58) Field of Classification Search .................. 585/648, 585/653, 649, 650, 906, 910
See application file for complete search history.

(56) References Cited

U.S. PATENT DOCUMENTS

| | | | |
|---|---|---|---|
| 5,314,610 A | 5/1994 | Gartside | |
| 5,348,642 A | 9/1994 | Serrand et al. | |
| 5,534,135 A | 7/1996 | Dai et al. | |
| 5,637,207 A | 6/1997 | Hsing et al. | |
| 5,702,589 A | 12/1997 | Tsang et al. | |
| 5,972,205 A | 10/1999 | Tsang et al. | |
| 6,045,690 A | 4/2000 | Fujiyama et al. | |
| 6,049,017 A | 4/2000 | Vora et al. | |
| 6,303,839 B1 | 10/2001 | Marker | |
| 6,307,117 B1 | 10/2001 | Tsunoda et al. | |
| 6,358,486 B1 | 3/2002 | Shan et al. | |
| 6,809,055 B2 | 10/2004 | Overbeek et al. | |
| 6,930,219 B2 | 8/2005 | Shan et al. | |
| 7,087,155 B1 | 8/2006 | Dath et al. | |
| 7,268,265 B1 | 9/2007 | Stewart et al. | |
| 7,314,963 B2 | 1/2008 | Voskoboynikov et al. | |
| 7,375,257 B2 | 5/2008 | Dath et al. | |
| 7,591,992 B2 | 9/2009 | Peng et al. | |

OTHER PUBLICATIONS

International Search Report and Written Opinion issued Oct. 11, 2010 in corresponding International application No. PCT/US2010/027184 (6 pages).
Office Action issued Jul. 31, 2012 in corresponding Canadian application No. 2,748,570 (2 pages).

*Primary Examiner* — Thuan D Dang
(74) *Attorney, Agent, or Firm* — Osha • Liang LLP

(57) ABSTRACT

Disclosed is a process for the production of C2 to C3 olefins via the catalytic cracking of feedstocks including C4 and heavier olefins in an integrated reaction/regeneration system.

24 Claims, 5 Drawing Sheets

PROCESS FOR THE PRODUCTION OF OLEFINS

CROSS-REFERENCE TO RELATED APPLICATION

This application, pursuant to 35 U.S.C. §119(e), claims priority to U.S. Provisional Application Ser. No. 61/162,074, filed Mar. 20, 2010. That application is incorporated by reference in its entirety.

BACKGROUND OF DISCLOSURE

1. Field of the Disclosure

Embodiments disclosed herein relate to processes where the reactors have a relatively short effective operating cycle length wherein the catalyst activity is limited by fouling and require frequent regeneration. Embodiments disclosed herein specifically relate to the production of C2 to C3 olefins via the catalytic cracking of feedstocks including C4 and heavier olefins.

2. Background

In the processing of hydrocarbons, there are numerous catalytic processes where the catalyst fouls in time periods such that frequent regeneration is necessary. One example is the catalytic cracking of feedstocks where, in typical fluid bed systems, the catalyst loses activity in a time frame measured in minutes to hours depending upon conditions. In order to re-establish the activity of the catalyst, the coke produced in the reaction, which reduces the activity of the catalyst, must be removed under controlled conditions so as to avoid excessive temperature that would then sinter the catalyst and thus render it inactive.

As the length of time for the operating cycle decreases due to the fouling of the catalyst, the operator has limited choices. One option is to employ a fluid bed or equivalent reactor where a portion of the catalyst is withdrawn continually and regenerated in a separate vessel. This type of system, however, is costly. A second option is to use a series of fixed bed reactors where a portion of the reactors are operating and another portion are regenerating. These reactor systems operate in a cyclic manner where as one reactor fouls, one recently regenerated is brought on line while the fouled reactor is simultaneously taken offline to regenerate spent catalyst. However, these systems typically require numerous pieces of equipment specifically for regeneration service and other equipment for providing the heat of reaction.

One specific example where this becomes an issue is in the cracking of moderate carbon number olefins to lower olefins, specifically ethylene and propylene. Catalytic cracking is routinely used to convert heavier petroleum fractions such as gas oils and residual fractions to lighter products, and fluidized catalytic cracking ("FCC") is particularly advantageous for heavy feeds. FCC is typically limited to feedstocks that produce sufficient coke on the catalyst, which when burned, generates sufficient heat to provide the necessary heat of reaction. The heavy feed contacts an appropriate catalyst and is cracked to form lighter products. The light products are typically gasoline and diesel oils, but fluid bed systems have been used to produce light olefins from heavy feeds.

Production of light olefins, for example, may also be effected by the catalytic cracking of moderate carbon number (C4 to C9) olefins. For example, C4 to C9 hydrocarbons may be cracked to form ethylene and propylene, among other products. Under these conditions, however, the amount of coke produced from these lighter feedstocks, is insufficient to overcome the endothermic heat of reaction, and separate heaters are required. In these cases additional equipment is required.

A variety of processes exist for the cracking of moderate carbon number olefins to produce lighter olefins, such as ethylene and propylene. However, such processes generally utilize conventional systems for feed preparation, reaction, and regeneration. For example, reactor systems, such as disclosed in U.S. Pat. Nos. 7,087,155 and 6,307,117, generally include use of two fixed bed reactor systems, where one reactor is operating and one reactor is regenerating. In these cases, separate operating equipment is required for the reaction systems and the regeneration systems.

Many recent endeavors to improve the cracking processes have investigated improvements to the catalysts used. However, conventional processes for the cracking of olefins, regardless of catalyst, often result in significant swings in product composition and conversion due to changes in catalyst performance over an operating cycle. Additionally, convention systems for feed preparation, reaction, and regeneration generally include multiple gas-fired heaters used for i) regeneration of the cracking catalysts and ii) heating of the feed to the cracker. Further, feed preparation systems typically utilize fixed bed hydrogenation systems to remove more highly unsaturated compounds, such as dienes, prior to entering the reactor. These systems typically operate in liquid phase and the resultant feed requires vaporization in additional equipment prior to entering preheating the feed for the reactor.

Accordingly, there exists a need for processes for the production of light olefins that may reduce the necessary operating costs and capital costs (e.g., process equipment piece count).

SUMMARY OF THE DISCLOSURE

In one aspect, embodiments disclosed herein relate to integration of the reaction and regeneration processes of a series of fixed bed reactor systems, where the catalyst requires regeneration with sufficient frequency. Multiple reactors are used in a cyclic operation/regeneration cycle. In these embodiments, the process includes: preheating a hydrocarbon feed stream with a regeneration gas via indirect heat exchange; feeding the preheated hydrocarbon feed stream to at least one operating reactor containing a catalyst; feeding the regeneration gas to a second reactor containing a catalyst undergoing regeneration; recovering at least a portion of the regeneration gas from the second reactor; feeding the recovered regeneration gas through a heat recovery system to reheat the recovered regeneration gas; and feeding the reheated recovered regeneration gas to the preheating as the regeneration gas. In some embodiments, the regeneration gas comprises at least one of nitrogen, oxygen, and combinations thereof. In further embodiments, the second reactor regenerates catalyst by combusting the coke that has fouled the catalyst. This process provides for the elimination of separate heating systems for hydrocarbon and regeneration gas and efficiently recovers heat from the circulating regeneration gas.

In another aspect, embodiments disclosed herein relate to a process for the production of light olefins. The process may include: feeding a hydrocarbon stream comprising C4 to C6 olefins to a cracking reaction zone comprising at least four reactors operated in a staggered reaction/regeneration cycle; contacting at least a portion of the C4 to C6 olefins with a catalyst in one or more of the reactors of the cracking reaction zone operating in a reaction cycle to crack at least a portion of the C4 to C6 olefins to form C2 to C3 olefins; recovering an effluent from the cracking reaction zone comprising the C2 to C3 olefins and unreacted C4 to C6 olefins; separating the effluent from the cracking reaction zone into at least two fractions including one or more fractions comprising at least one of C2 hydrocarbons, C3 hydrocarbons, and a combination thereof, and one or more fractions comprising at least one of C4 hydrocarbons, C5 hydrocarbons, C6 hydrocarbons, and a combination thereof; contacting the hydrocarbon stream with a regeneration gas in indirect heat exchange to increase a temperature of the hydrocarbon stream prior to the contacting at least a portion of the C4 to C6 olefins with a catalyst in reactors of the cracking reaction zone in a reaction cycle; feeding the regeneration gas and at least one of oxygen and air to one or more of the reactors in the cracking reaction zone operating in a regeneration cycle to regenerate the catalyst contained therein; recovering a regeneration gas effluent comprising combustion products from the reactors in the cracking reaction zone in a regeneration cycle; withdrawing at least a portion of the recovered regeneration gas effluent comprising combustion products as a purge; combining at least a portion of the regeneration gas effluent with make-up nitrogen to form a mixed regeneration gas; heating the compressed mixed regeneration gas to a temperature in the range from about 600° C. to about 1000° C.; and feeding the heated mixed regeneration gas to the cracking reaction zone as the regeneration gas.

In other aspects, embodiments disclosed herein relate to a process for the production of light olefins, including: feeding hydrogen and a C4 to C6 hydrocarbon stream comprising dienes and olefins to a first reaction zone comprising a catalytic distillation reactor system containing a selective hydrogenation catalyst; concurrently in the catalytic distillation reactor system: contacting hydrogen and C4 to C6 dienes with the selective hydrogenation catalyst to selectively hydrogenate C4 to C6 dienes to form additional olefins; recovering an effluent from the catalytic distillation reactor system comprising the C4 to C6 olefins and the additional olefins; feeding at least a portion of the effluent from the catalytic distillation reactor system to a second reaction zone, wherein the second reaction zone comprises at least four reactors operated in a staggered reaction/regeneration cycle; contacting at least a portion of the effluent from the catalytic distillation reactor system with a catalyst in one or more reactors of the second reaction zone operating in a reaction cycle to crack at least a portion of the C4 to C6 olefins to form C2 to C3 olefins; recovering an effluent from the second reaction zone comprising the C2 to C3 olefins and unreacted C4 to C6 olefins; separating the effluent from the second reaction zone into at least two fractions including one or more fractions comprising at least one of C2 hydrocarbons, C3 hydrocarbons, and a combination thereof, and one or more fractions comprising at least one of C4 hydrocarbons, C5 hydrocarbons, C6 hydrocarbons, and a combination thereof; recycling at least a portion of the one or more fractions comprising C4 hydrocarbons, C5 hydrocarbons, C6 hydrocarbons, and a combination thereof to the first reaction zone; contacting the effluent from the catalytic distillation reaction system with a regeneration gas in indirect heat exchange to increase a temperature of the effluent prior to the contacting of at least a portion of the effluent from the catalytic distillation reactor system with a catalyst in one or more reactors of the second reaction zone operating in a reaction cycle; and feeding the regeneration gas after indirect heat exchange and at least one of oxygen and air to one or more reactors in the second reaction zone operating in a regeneration cycle to regenerate the catalyst contained therein; contacting the effluent from the catalytic distillation reaction system with the effluent from the reactors operating in the reaction cycle in the second reaction zone in indirect heat exchange to increase a temperature of the effluent from the catalytic distillation reaction system prior to the contacting the effluent from the catalytic distillation reaction system indirectly with the regeneration gas; recovering a regeneration gas effluent comprising combustion products from the reactors in the second reaction zone in a regeneration cycle; withdrawing at least a portion of the recovered regeneration gas effluent comprising combustion products as a purge; combining at least a portion of the regeneration gas effluent with make-up nitrogen to form a mixed regeneration gas; compressing the mixed regeneration gas; contacting the regeneration gas effluent in indirect heat exchange with the compressed mixed regeneration gas; heating the compressed mixed regeneration gas to a temperature in the range from about 600° C. to about 1000° C.; and feeding the heated mixed regeneration gas to the second reaction zone as the regeneration gas.

In other aspects, embodiments disclosed herein relate to a process for the production of light olefins, including: feeding hydrogen and a C5 hydrocarbon stream comprising C5 dienes, C5 olefins and cyclopentadiene to a first reaction zone comprising a catalytic distillation reactor system containing a selective hydrogenation catalyst; concurrently in the catalytic distillation reactor system: contacting hydrogen and C5 dienes with the selective hydrogenation catalyst to selectively hydrogenate C5 dienes to form additional olefins and hydrogenate at least a portion of the cyclopentadiene to cyclopentene; recovering an effluent from the catalytic distillation reactor system comprising the C5 olefins and the additional olefins; recovering a bottoms fraction from the catalytic distillation reactor system comprising cyclopentene; feeding at least a portion of the effluent from the catalytic distillation reactor system to a second reaction zone, wherein the second reaction zone comprises at least four reactors operated in a staggered reaction/regeneration cycle; contacting at least a portion of the effluent from the catalytic distillation reactor system with a catalyst in one or more reactors of the second reaction zone operating in a reaction cycle to crack at least a portion of the C5 olefins to form C2 to C3 olefins; recovering an effluent from the second reaction zone comprising the C2 to C3 olefins and unreacted C5 olefins; separating the effluent from the second reaction zone into at least two fractions including one or more fractions comprising at least one of C2 hydrocarbons, C3 hydrocarbons, and a combination thereof, and a fraction comprising C5 hydrocarbons; recycling at least a portion of the fraction comprising C5 hydrocarbons to the first reaction zone; contacting the effluent from the catalytic distillation reaction system with a regeneration gas in indirect heat exchange to increase a temperature of the effluent prior to the contacting of at least a portion of the effluent from the catalytic distillation reactor system with a catalyst in one or more reactors of the second reaction zone operating in a reaction cycle; and feeding the regeneration gas and at least one of oxygen and air to one or more reactors in the second reaction zone operating in a regeneration cycle to regenerate the catalyst contained therein; contacting the effluent from the catalytic distillation reaction system with the effluent from the second reaction zone in a reaction cycle in indirect heat exchange to increase a temperature of the effluent from the catalytic distillation reaction system prior to the contacting the effluent from the catalytic distillation reaction system indirectly with the regeneration gas; recovering a regeneration gas effluent comprising combustion products from the reactors in the second reaction zone in a regeneration cycle; withdrawing at least a portion of the recovered regeneration gas effluent comprising combustion products as a purge; combining at least a portion of the regeneration gas effluent with make-up nitrogen to form a mixed regeneration gas; compressing the mixed regeneration gas; contacting the regeneration gas effluent with the compressed mixed regeneration gas; heating the compressed mixed regeneration gas to a temperature in the range from about 600° C. to about 1000° C.; and feeding the heated mixed regeneration gas to the second reaction zone as the regeneration gas.

Other aspects and advantages will be apparent from the following description and the appended claims.

BRIEF DESCRIPTION OF DRAWINGS

FIGS. 1 and 3-6 are each illustrated as simplified flow diagrams; one skilled in the art will recognize that other components not illustrated may be present, including valves, control valves, pumps, filters, motors, control equipment, and pressure, temperature, and flow measurement devices, among other components.

DETAILED DESCRIPTION

Figure 1:
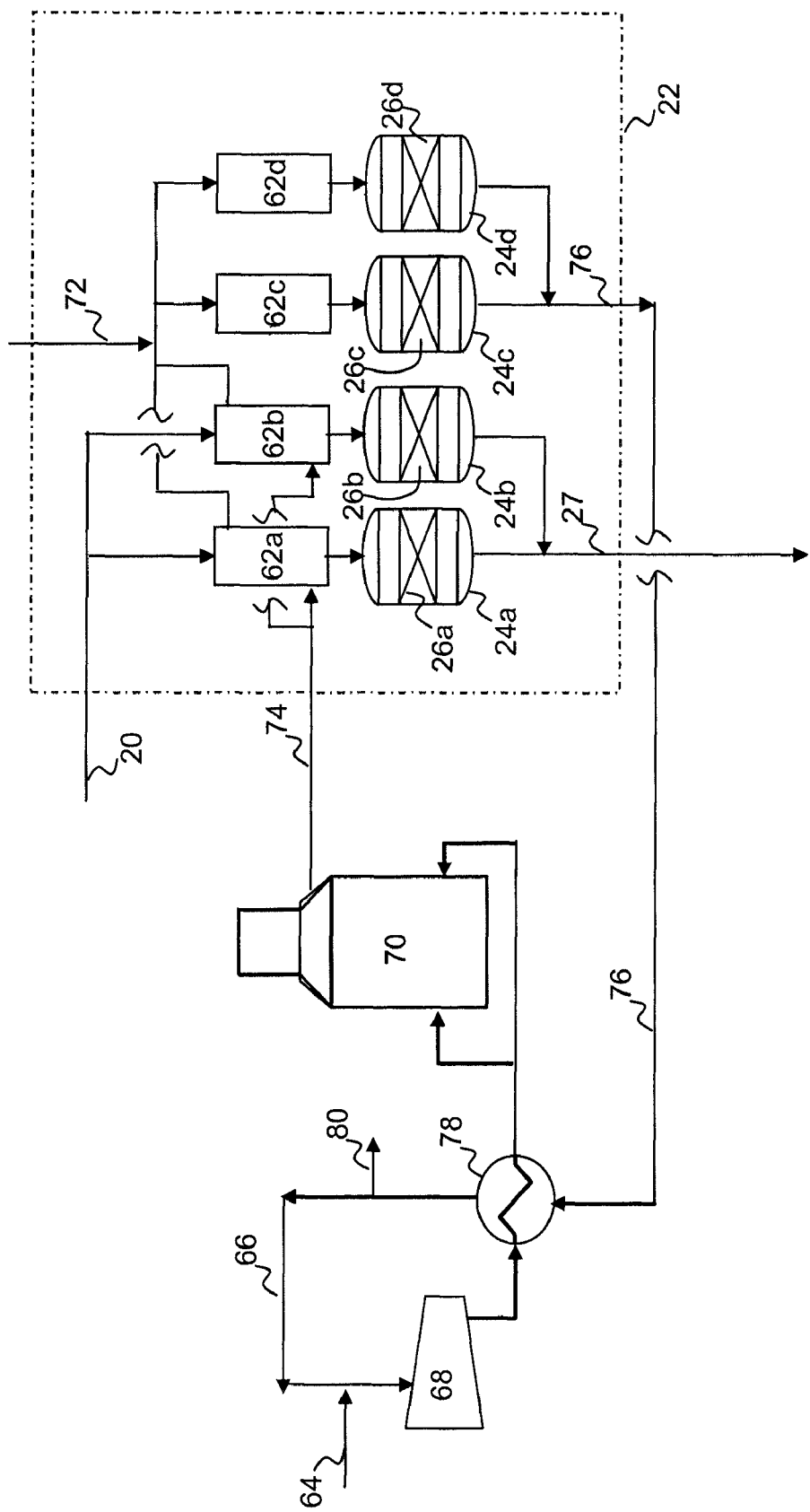
FIG. 1 illustrates a process for the production of olefins according to embodiments disclosed herein.

The production of olefins is described herein as from the catalytic cracking of moderate carbon number olefins. However one of skill in the art would appreciate that the advantages described herein are applicable to other reaction systems where the combination of operating reactors and regenerating reactors are required to achieve steady state operation.

In one aspect, embodiments disclosed herein relate to the production of C2 to C3 olefins via the catalytic cracking of feedstocks including C4 and heavier olefins. In other aspects, embodiments disclosed herein relate to the production of C2 to C3 olefins via the catalytic cracking of feedstocks including C4 and heavier olefins in an integrated reaction/regeneration system. In other aspects, embodiments disclosed herein relate to the production of C2 to C3 olefins via the catalytic cracking of feedstocks including C4 and heavier olefins in an integrated reaction/regeneration system, where a mass balanced regeneration system may be used to provide the heat necessary for the endothermic cracking reaction. As used herein, "mass balanced" may refer to steady state, pseudo steady state, or similar operating conditions as may be sustained during normal operation of a chemical process. In another aspect, embodiments disclosed herein relate to use of a multiple reactor system for performing the cracking reaction, where the multiple reactors may be operated in a staggered reaction/regeneration cycle to reduce variations in conversion and product composition commonly associated with two-reactor systems.

In other aspects, embodiments disclosed herein relate to the production of C2 to C3 olefins via the selective hydrogenation of diolefins that may be contained in a hydrocarbon feedstock including C4 and heavier olefins followed by the catalytic cracking of the C4 and heavier olefins. In some embodiments, at least a portion of the selective hydrogenation of diolefins may be performed in a catalytic distillation reactor system.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein. Catalytic distillation reactor systems according to embodiments disclosed herein may be used in conjunction with one or more upstream and/or downstream reactors to achieve the desired conversion and separation.

Feedstocks to processes disclosed herein may include any kind of olefin-containing hydrocarbon stream. The feedstock may typically include from 10 to 100 weight percent olefins and diolefins, and may be fed to processes according to embodiments disclosed herein undiluted or diluted by a diluent, such as a non-olefinic hydrocarbon or nitrogen. In some embodiments, olefin-containing feedstocks may include a hydrocarbon mixture containing normal and branched olefins in the range from C4 to C10 hydrocarbons; in the range from C4 to C9 hydrocarbons in other embodiments; in the range from C4 to C6 hydrocarbons in other embodiments; and C4 hydrocarbons, C5 hydrocarbons, C6 hydrocarbons, or mixtures thereof in other embodiments. In some embodiments, the olefin-containing feedstock may include a C5 hydrocarbon fraction including one or more of linear, branched, and cyclic C5 olefins, and linear, branched, and cyclic C5 diolefins, including cyclopentadiene. As mentioned above, feedstocks disclosed herein may include any kind of olefin-containing hydrocarbon stream; while embodiments disclosed herein may be limited to C4 to C6, C9, or C10 hydrocarbons, one skilled in the art would recognize that hydrocarbons of carbon number greater than C6, C9, or C10 may be processed in a similar manner.

Furthermore, the present invention is compatible with the reaction of non-olefin containing streams to end products Such reaction systems include, but are not limited to the following:

a) The reaction of methanol to olefins where the methanol forms light olefins and water over zeolitic catalysts. Catalyst fouling is an issue and the process typically takes place in a fluid bed.

b) The cracking of non-olefinnic paraffin streams to olefins where the endothermic heat of reaction is high and thus more extensive feed preheat is required Hydrocarbon feedstocks useful in the olefin cracking processes disclosed herein may come from a variety of sources, such as from refineries, byproduct streams from oxygenate reaction systems such as Methanol to Olefins (MTO) processes, and steam cracking units. For example, a C4 cut from a Fluid Catalytic Cracking (FCC) unit may include around 50 weight percent olefins. Feedstocks may also include diene rich C4 and/or C5 cuts, typically containing greater than 40 or 50 weight percent dienes and olefins. Alternatively, feedstocks may include a pure olefinic or diolefinic feedstock which has been produced in a petrochemical plant.

In some embodiments, the use of a fraction including C5 hydrocarbons may be advantageous due to the removal of the C5 hydrocarbons from the gasoline pool, for example. The content of C5 hydrocarbons in gasoline is generally limited based on the allowable Reed Vapor Pressure (RVP) of the gasoline, which may also be affected by any added ethanol. Accordingly, embodiments disclosed herein may advantageously convert C5 hydrocarbons, including olefins, into valuable lighter C2 and C3 olefins, thus providing an alternative outlet to gasoline for the C5 hydrocarbons.

The above described olefin-containing hydrocarbon feedstocks may be fed to a reaction zone for catalytically cracking of the feed to form light olefins, such as ethylene and propylene. Reaction zones for catalytically cracking hydrocarbon feedstocks according to embodiments disclosed herein may include multiple fixed bed reactors, such as four or more reactors in parallel, each including one or more beds of a catalytic cracking catalyst. The multiple reactors advantageously provide for operation of the reactors in a staggered reaction/regeneration cycle. Additionally, the reactors in a regeneration cycle may be regenerated using an integrated regeneration gas system. The staggered operation and integrated regeneration gas system are described in detail below.

The above described feedstocks may alternatively be first fed to a first reaction zone where the feed is contacted with hydrogen in the presence of a selective hydrogenation catalyst to selectively convert dienes contained within the feedstocks to olefins. Hydrogen flow rates to the selective hydrogenation reactor may be staged (fed at multiple points along the reactor) or otherwise controlled to limit the conversion of olefins to paraffins. In some embodiments, a diene rich feedstock may be hydrogenated to result in a hydrocarbon stream containing olefins. In other embodiments, such as where dienes are a minor component in a hydrocarbon feedstock, the feedstocks may be selectively hydrogenated to reduce the content of the highly-reactive dienes. The effluent from this first reaction zone may then be fed to a second reaction zone where the effluent is subjected to catalytic cracking.

Catalysts useful for the catalytic cracking of olefin-containing streams according to embodiments disclosed herein may include any suitable catalytic cracking catalyst, including zeolitic and non-zeolitic catalysts. For example, the cracking reaction may be performed in the presence of a crystalline zeolitic catalyst in some embodiments, ZSM-5 zeolitic catalyst in other embodiments, and in the presence of a ZSM-5 zeolitic catalyst with a Si/Al ratio of greater than 50 in some embodiments, and a Si/Al ratio of greater than 200 in yet other embodiments.

Various catalysts for the cracking of hydrocarbons are disclosed in U.S. Pat. Nos. 7,375,257, 7,314,963, 7,268,265, 7,087,155, 6,358,486, 6,930,219, 6,809,055, 5,972,205, 5,702,589, 5,637,207, 5,534,135, and 5,314,610, among others. Each of the aforementioned patents is hereby incorporated by reference.

Cracking of the olefins may be performed at appropriate conditions to result in the desired product distribution (e.g., favoring propylene, favoring ethylene, etc.). The process operating conditions typically employ a high space velocity, a low pressure, and a high reaction temperature. Liquid hourly space velocities (LHSV) of the feed through the reactor may be within the range from $10\ h^{-1}$ to $30^{-1}$ for example. The olefin partial pressure may be within the range from about 0.1 to about 2 bar; the total absolute pressure in the reactor may be within the range from about 0.1 to about 20 bar. The cracking of the olefins may be performed at an inlet temperature in the range from about 400° C. to about 700° C. in some embodiments; from about 450° C. to about 650° C. in other embodiments; from about 500° C. to about 600° C. in other embodiments; and from about 525° C. to about 590° C. in yet other embodiments.

The cracker effluent may include C2 olefins, C3 olefins, and unreacted C4+ olefins, among other products. Effluent from the cracking reactor may be sent to a separation system to separate the cracker effluent into carbon number groups by technology well known in the art. For example, products from the cracking unit may include ethylene, propylene, C4s, C5s, C6s, as well as various aromatics, which may be separated, for example, using one or more of a deethanizer, a depropanizer, a debutanizer, a depentanizer, and other similar fractionation columns to result in the desired product streams. In some embodiments, the cracker effluent may be separated into at least two fractions including one or more fractions comprising at least one of C2 hydrocarbons, C3 hydrocarbons, and a combination thereof, and one or more fractions comprising at least one of C4 hydrocarbons, C5 hydrocarbons, C6 hydrocarbons, and a combination thereof. The C4+ hydrocarbons, or a portion thereof, may be recycled to various portions of processes according to embodiments disclosed herein for further processing.

Referring now to FIG. 1, a process for the production of olefins according to embodiments disclosed herein is illustrated. The hydrocarbon feedstock is fed via flow line 20 to cracking reaction zone 22, which includes four catalytic cracking reactors 24a, 24b, 24c, and 24d, each containing one or more beds 26a, 26b, 26c, and 26d of catalytic cracking catalyst. The catalytic cracking reactors 24a-d, as illustrated, include two reactors in a reaction cycle (reactors 24a and 24b), and two reactors in a regeneration cycle (reactors 24c and 24d). The hydrocarbon feedstock fed via flow line 20 may be in the vapor phase, or may be vaporized prior to being fed to cracking reaction zone 22.

The hydrocarbon feed to cracking reaction zone 22 may be heated to the desired cracking reaction temperature via indirect heat exchange in exchangers 62a, 62b. To minimize heat loss, exchangers 62a, 62b, 62c, and 62d may be located proximate to or close-coupled to reactors 24a, 24b, 24c, and 24d, respectively. In other embodiments, exchangers 62a-d and reactors 24a-d may be integral reactor/exchangers providing for concurrent heating and feed distribution.

The olefins are contacted with catalyst in beds 26a, 26b and cracked to form light olefins, such as ethylene and propylene. An effluent including ethylene, propylene, and unreacted heavier olefins in the hydrocarbon feed may be recovered from reactors 24 via flow line 27 and fed to a separation system (not shown) to separate the cracker effluent into carbon number groups, as described above.

As noted above and illustrated in FIG. 1, the cracking reaction zone may include multiple reactors, and may include four or more reactors in some embodiments. The use of four or more reactors may allow the reactors 24a-d to be operated in a staggered reaction/regeneration cycle, providing for more consistent reactor performance, and less product composition variation, than a typical two-reactor system operating with one reactor operating and one reactor regenerating. For a system where the catalyst is deactivating due to fouling at a substantial rate (requiring frequent regeneration), the conversion achieved changes as the catalyst activity falls. This can place a substantial hardship on the design of the separation systems in order to be able to achieve product specification with a continually changing feedstock composition. The use of four reactors versus two minimizes this variation by staggering the starting times for each reactor. Additionally, use of four or more reactors in a staggered reaction/regeneration cycle according to embodiments disclosed herein may allow for use of advantageous reactor length to diameter ratios (L/D ratio), which may allow for better mixing, more consistent reactor operation, and reduction of the instantaneous regeneration gas requirements.

Figure 2:
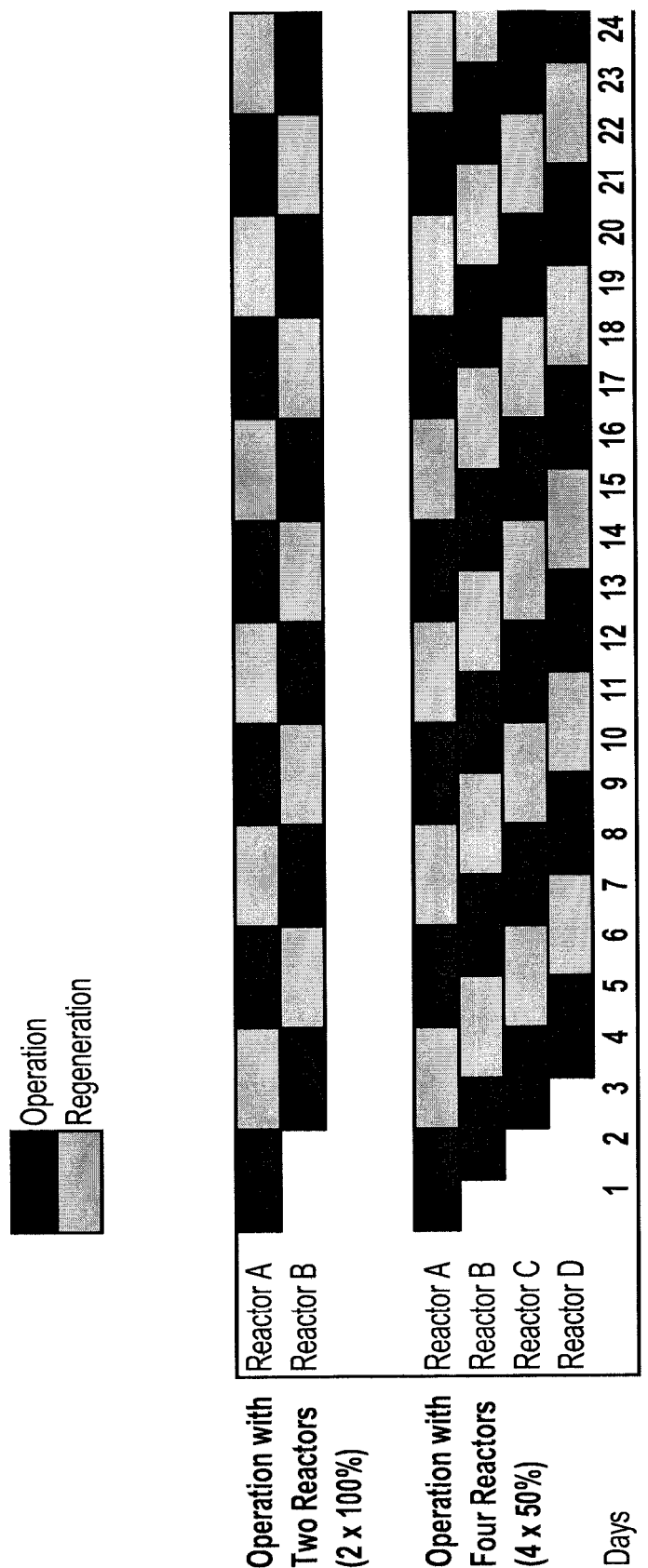
FIG. 2 compares a prior art two-reactor cyclic operation with a four-reactor system operating in a staggered reaction/regeneration cycle according to embodiments disclosed herein.

A staggered reaction/regeneration cycle according to embodiments disclosed herein is illustrated in FIG. 2, comparing the cyclic operation of four reactors with the cyclic operation of two reactors. The four reactor staggered reaction/regeneration cycle includes the concurrent operation of two reactors while two reactors are regenerating. The start time for the two operational reactors is staggered so as to have one reactor operating with partially spent catalyst and one reactor operating with fresh catalyst. For example, as illustrated in FIG. 2 for reactors having a catalyst cycle of about 2 days, a reactor is shut down and a reactor is brought on-line each day, resulting in one operational reactor having 1-day old catalyst and one operational reactor having fresh catalyst. In contrast, as comparatively illustrated in FIG. 2, a two-reactor system changes from spent catalyst to fresh catalyst upon change in operation from Reactor A to Reactor B every two days, potentially resulting in frequent swings in reactor performance and product composition. Although illustrated with regard to four reactors, similar staggered reaction/regeneration cycles may be readily envisioned for systems having more than four reactors. Additionally, although illustrated with respect to a catalyst cycle time of 2 days, cracking catalysts having cycle times of 10 days or more are commercially available.

Referring again to FIG. 1, the heat exchange medium used to heat the cracker feed may include hot regeneration gas supplied by an integrated regeneration gas system. Nitrogen fed via flow line 64 is introduced to the integrated regeneration gas system and combined with recirculating regeneration gas in stream 66. The combined regeneration gas may be compressed via compressor 68 and heated in regeneration gas heater 70 via indirect heat exchange to a temperature sufficient to i) provide final preheat of the hydrocarbon feed to reactors 62a, 62b that are in a reaction cycle, and ii) with oxygen or air added via flow line 72, regenerate the cracking catalyst in reactors 62c, 62d that are in a regeneration cycle. Hot regeneration gas may be fed via flow line 74 to exchangers 62a, 62b for the hydrocarbon feed preheating, and may then be admixed with air or oxygen fed via flow line 72 and passed through exchangers 62c, 62d to regenerate the catalyst in beds 26c, 26d. Passing the regeneration gas through exchangers 62c, 62d may additionally remove any buildup on the heat exchanger tubes. Use of regeneration gas in this manner may allow for the elimination of a fired heater for heating of a hydrocarbon feed upstream of crackers, as is typically used in prior art cracking processes. Heat duty requirements for heating of the hydrocarbon feed to the cracking reaction zone may additionally be met via use of appropriate heat exchange networks, including cracking reactor feed/effluent exchangers.

The amount of hot regeneration gas passed as a heat exchange medium through exchangers 62a, 62b may be controlled to result in the desired hydrocarbon inlet temperature to reactors 24a, 24b. Appropriate control valves and bypass lines may be included to route excess hot regeneration gas directly from heater 70 to exchangers 62c, 62d.

Addition of oxygen or air via flow line 72 may additionally be controlled to effect the catalyst regeneration within the time constraints of the staggered reaction/regeneration cycle. Oxygen content in the regeneration gas fed to reactors 24c, 24d may additionally be controlled to avoid excessive regeneration temperatures, minimize flammability concerns, and to maintain a stable operation of compressor 68. In some embodiments, the air or oxygen may be heated in heater 70, such as via use of two separate coils, one to heat the recirculating regeneration gas and one to heat the air or oxygen for admixture with the hot regeneration gas upstream of the exchangers and reactors to be regenerated. Alternatively, the air/oxygen in line 72 could be preheated by indirect heat exchange with the recycle regeneration gas in line 76.

Oxygen in the gas fed to the reactors being regenerated may react with (combust) coke and other deposits on the cracking catalyst, preheat exchangers 62a-d, tube walls, and vessel walls, forming various combustion products including water, carbon monoxide, and carbon dioxide. This system allows for the decoking of the preheater tubes on the same cyclic basis as the reactor catalyst, thus minimizing any potential for fouling in the final preheating step. The combustion products and the circulating regeneration gas may be recovered from reactors 24c, 24d via flow line 76 for recycle to compressor 68. Additional heat may be recovered from the effluent regeneration gas via indirect heat exchange with the compressed regeneration gas in heat exchanger 78. A purge stream may be taken from the recirculating regeneration gas via flow line 80 to purge water, carbon monoxide, carbon dioxide, and other combustion products, controlling buildup of the combustion products in the recirculating regeneration gas. The make-up nitrogen fed via flow line 64 may be balanced with the purge taken via flow line 80 in some embodiments. The regeneration gas in flow line 76 may be cooled to a temperature sufficient to condense and purge water from the circulating gas in some embodiments.

The above described integrated regeneration gas system may provide for relatively consistent mass flow rates through the regeneration system, allowing for control of reactor inlet temperatures and regeneration conditions, and minimization of the instantaneous regeneration gas requirements. This reduces the range of flows over which the regeneration gas compression system (compressor 68) must operate. This has a major impact on system control and operability. Further, this allows for the efficient recovery of heat from the regeneration gas as it leaves the reactor, as heat exchange can be designed for operation over a more defined and constant flow rate.

In some embodiments, it may be desired or necessary to hydrogenate dienes in the olefin-containing feedstocks prior to cracking according to embodiments as described above. The above described hydrocarbon feedstocks may be fed to a selective hydrogenation reaction zone where the feed is contacted with hydrogen in the presence of a selective hydrogenation catalyst to selectively convert dienes contained within the feedstocks to olefins. Hydrogen flow rates to the selective hydrogenation reactor may be staged (fed at multiple points along the reactor) or otherwise controlled to limit the conversion of olefins to paraffins. In some embodiments, a diene rich feedstock may be hydrogenated to result in a hydrocarbon stream containing olefins. In other embodiments, such as where dienes are a minor component in a hydrocarbon feedstock, the feedstocks may be selectively hydrogenated to reduce the content of the highly-reactive dienes.

Feedstocks containing dienes may be selectively hydrogenated to result in an olefin-containing hydrocarbon stream having a diene content of less than about 1 weight percent dienes; less than about 500 ppm dienes in other embodiments; less than about 250 ppm dienes in other embodiments; less than about 100 ppm dienes in other embodiments; less than about 50 ppm dienes in other embodiments; and less than about 10 ppm dienes in yet other embodiments.

Catalysts useful for the selective hydrogenation of dienes according to embodiments disclosed herein may include any selective hydrogenation catalyst. Among the metals known to catalyze the hydrogenation reaction are platinum, rhenium, cobalt, molybdenum, nickel, tungsten, ruthenium, copper, and palladium, among others. For example, the hydrogenation catalyst may include substantially any catalyst capable of catalyzing the hydrogenation of benzene to cyclohexane. Catalysts useful for the selective hydrogenation of acetylene to ethylene typically contain one or more metals selected from Group VIII of the Periodic Table, such as palladium, ruthenium, platinum, nickel, etc., or catalysts containing one or more noble metals, such as silver. In some embodiments, the Group VIII catalyst or mixture of Group VIII catalysts may be co-formulated with other metals, such as those from Groups I through VII, and may be support on silica, alumina, alumina-silica, and other various supports. For example, Group VIII metals of the Periodic Table of Elements, such as platinum and palladium may be used as the principal catalytic component, alone or with promoters and modifiers such as palladium/gold, palladium/silver, and cobalt/zirconium. Such catalysts may be deposited on a support, such as alumina, fire brick, pumice, carbon, resin, silica, an aluminosilicate, such as a zeolite or the like. Generally, commercial forms of catalyst use supported oxides of these metals. The oxide is reduced to the active form either prior to use with a reducing agent or reduced during use by the hydrogen in the feed. Specific examples of hydrogenation catalysts useful in embodiments herein include platinum on alumina and platinum on a zeolite with alumina binder added for strength. Suitable zeolites include X, Y, faujasite, mordenite, and synthetic aluminosilicates, among others.

When used in a catalytic distillation reactor system, to facilitate fractionation and catalytic activity, the above described catalysts may be prepared in the form of a distillation structure. The catalytic distillation structure must be able to function as catalyst and as mass transfer medium. The catalyst must be suitably supported and spaced within the column to act as a catalytic distillation structure.

Conditions for selective hydrogenation include temperatures in the range from about 50° F. to about 420° F. in some embodiments; from about 55° F. to about 380° F. in other embodiments; and from about 60° F. to about 300° F. in yet other embodiments. The temperature of operation used may depend upon the specific compounds to be hydrogenated and the physical phase of the hydrocarbons in a specific catalytic reaction zone, and may vary for liquid phase reaction systems, vapor phase reaction systems, or mixed phase reaction systems as may occur in catalytic distillation reactor systems and boiling point reactors. Pressures in the reaction zone may likewise depend upon the feed components and the phase of operation, but are typically in the range from about 0 to about 350 psig. For selective hydrogenation of C4 and C5 dienes, for example, the temperature may be in the range from about 50° F. to about 250° F. in some embodiments. The concentration of hydrogen in the catalytic reaction zone depends on a number of factors; including the concentration of dienes in the incoming feed stream into a specific reaction zone, the specific diene compounds (which may vary in reactivity), the intended conversion of dienes across a specific catalytic reaction zone, the hydrocarbon phase of the catalytic reaction zone (i.e., single phase or mixed phase), the temperature of a specific catalytic reaction zone, catalyst composition in a specific reaction zone, and the specific physical device of the catalytic reaction zone, such as a fixed bed reactor, ebullating or fluidized bed reactor, or catalytic distillation column reactor. In general, the minimum amount of hydrogen is no less than 40 mole % of the concentration of the total dienes in the incoming stream into a specific catalytic reaction zone. The maximum amount of hydrogen used in a catalytic reaction zone in fixed bed operations is typically no higher than 5 times the moles of total acetylenic compounds. In general, more hydrogen is needed for the catalytic distillation operation than the fixed bed operation.

The selective hydrogenation of the dienes in the feedstock may typically be accomplished without substantial conversion of olefins in the feedstock to paraffins. For example, the olefin-content of the feed may be reduced during selective hydrogenation by less than 25 mole % in some embodiments; less than 20 mole % in other embodiments; less than 15 mole percent in other embodiments; less than 10 mole % in other embodiments; less than 5 mole % in other embodiments; and less than 1 mole % in yet other embodiments.

The reaction zone for selective hydrogenation of the dienes may include a catalytic distillation reactor system in some embodiments. In other embodiments, the reaction zone for selective hydrogenation of the dienes may include one or more fixed bed reactors, moving bed reactors, or fluidized bed reactors in series with a catalytic distillation reactor system. The feedstock may be selectively hydrogenated in the catalytic distillation reactor system, and the C4+ olefins, or a portion thereof, may be recovered from the catalytic distillation reactor system.

The olefin-containing effluent may be recovered from the catalytic distillation reactor system as an overhead fraction or as a side draw. The overhead fraction or side draw may be recovered as a vapor phase, liquid phase, or a combination thereof. In some embodiments, such as where a minor amount of hydrogen may be tolerated in the cracker and other downstream processes, the overhead fraction or side draw may be recovered as a vapor phase draw, which may reduce or eliminate downstream heating requirements typically required to vaporize the feed to the cracker.

In some embodiments, such as for a C5 diene rich feedstock including linear and branched C5 dienes as well as cyclopentadiene, a large amount of heat may be released during hydrogenation of the diene-rich streams. Catalytic distillation reactor systems may advantageously provide for efficient heat removal during the hydrogenation process. In some embodiments, at least a portion of the cyclopentadienes may be hydrogenated to cyclopentenes in the catalytic distillation reactor system and/or any upstream hydrogenation reactors, recovered in the bottoms fraction. Additionally, cyclic components, including, for example, cyclopentane, cyclopentene, and cyclopentadiene, may be separated from the olefins and recovered as a bottoms fraction from the catalytic distillation reactor system, thus removing at least a portion of the cyclic hydrocarbons from downstream processes. Cyclic olefins are typically less reactive over cracking catalysts than the linear or branched components and thus removing them prior to the cracking reactor(s) will improve the efficiency of the cracking reaction section.

It is a further advantage of incorporating such a fractionation step (with or without catalytic distillation functionality in the tower) following the hydrogenation to allow for the vaporization of the olefinic feed to the reactor section. Vaporization of highly olefinic feeds to temperatures required for cracking create the potential for fouling of the heat transfer equipment. Vaporization of these feeds in the tower considerably reduces such fouling by limiting the temperatures of surfaces for vaporization that would commonly occur in equipment such as fired heaters or tubular exchangers heated by hot steam.

Figure 3:
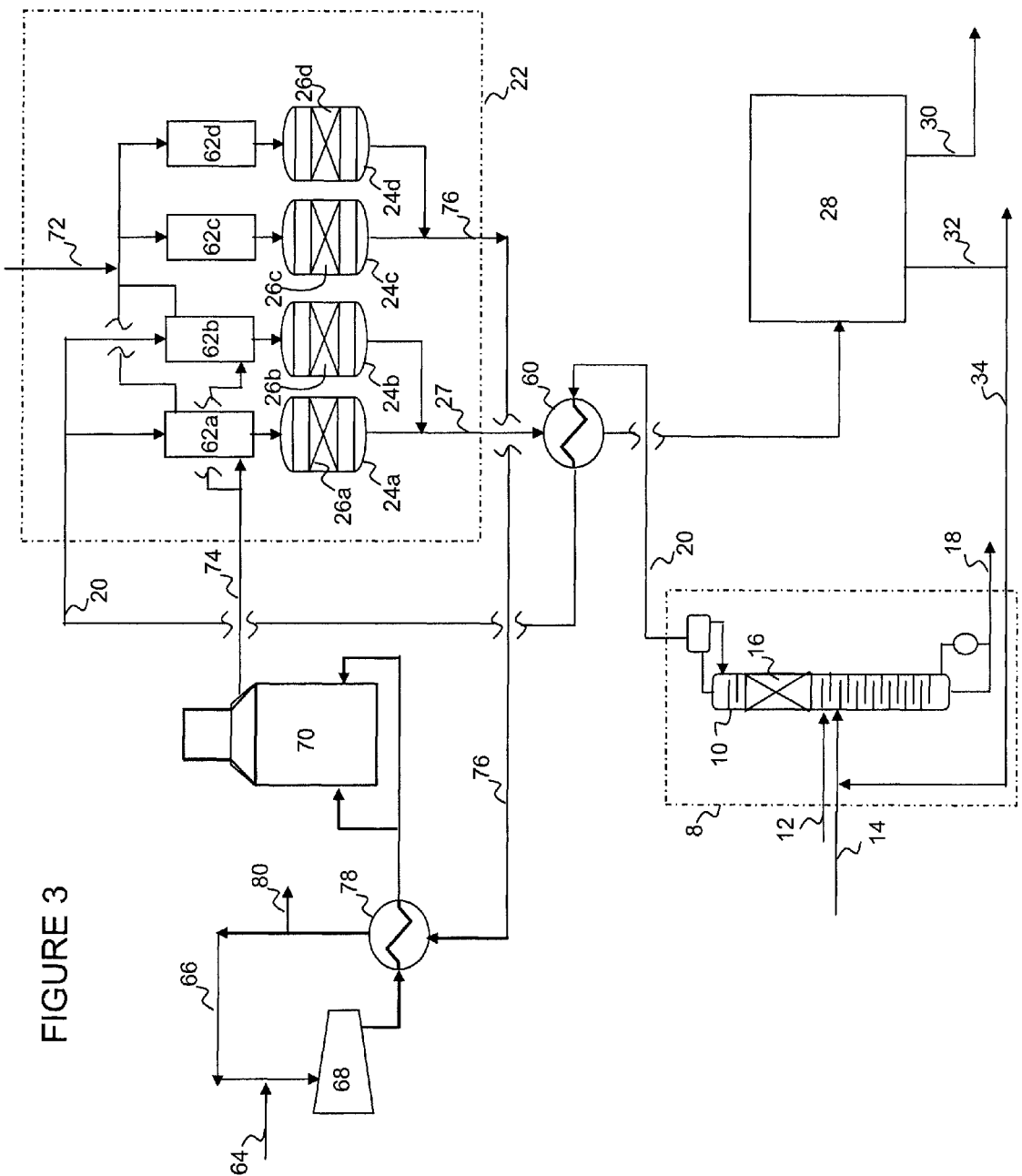
FIG. 3 illustrates a process for the production of olefins according to embodiments disclosed herein.

Referring now to FIG. 3, a process for the production of olefins according to embodiments disclosed herein is illustrated, where like numerals represent like parts. Hydrogen and a hydrocarbon feedstock as described above including olefins and diolefins are fed to a selective hydrogenation reaction zone 8 including a catalytic distillation reactor system 10 via flow lines 12 and 14, respectively. Catalytic distillation reactor system 10 may include one or more beds 16 of selective hydrogenation catalyst, where the beds 16 may contain the same or different catalysts. In catalytic distillation reactor system 10, higher boiling components traverse downward through the column and may be recovered via flow line 18. Lighter boiling components, including hydrogen, olefins, and diolefins, traverse upward through the column, contacting the selective hydrogenation catalyst, converting at least a portion of the diolefins to olefins. In this embodiment, the lighter boiling components, having a reduced diene content as compared to the feed hydrocarbons, may be recovered from catalytic distillation reactor system 10 as an overhead vapor fraction via flow line 20, thus negating the need for vaporization of the olefin-containing feed prior to cracking, as described above.

Depending upon the specific concentration of diolefins and/or acetylenics present in the hydrocarbon feed, it may be advantageous to locate one or more beds 16 of selective hydrogenation catalyst within catalytic distillation reactor system 10 below the feed point. Note that catalyst beds 16 may be above and/or below the feed point and that hydrogen fed to catalytic distillation reactor system 10 may be split with feed points located along the length of the tower.

The overhead vapor fraction, preferably in a vapor phase, may be fed via flow line 20 to a cracking reaction zone 22, which may include multiple reactors 24 containing one or more beds 26 of a catalytic cracking catalyst. The overhead vapor draw recovered from column 10 via flow line 20 may be heated in heat exchanger 60 via indirect heat exchange with cracking reaction zone effluent 27, recovering heat from the reactor effluent stream. Alternatively, if the product from column 10 is a liquid product, then heat exchanger 60 can be used to vaporize the stream which is then fed to exchangers 62 (*a-b*) for final preheating. As described above, the overhead fraction may then be heated to temperatures sufficient for the cracking reaction via indirect heat exchange in one or more heat exchangers 62. The olefins are then cracked to form light olefins, such as ethylene and propylene, and an effluent including ethylene, propylene, and unreacted heavier olefins in the hydrocarbon feed may be recovered from reactors 24 via flow line 27. Effluent from the cracking reactor may be sent via flow line 27 to a separation system 28 to separate the cracker effluent into carbon number groups, as described above. As illustrated in FIG. 3, two fractions are recovered from separation system 28, including a fraction containing the light olefins (C2s and C3s), which may be recovered via flow line 30, and a fraction containing the unreacted heavy olefins (C4+), which may be recovered via flow line 32.

In some embodiments, at least a portion of the fraction containing the heavy olefins may be recycled via flow line 34 to the selective hydrogenation reaction zone 8 for further processing. Fractionation columns used in separation system 28 may additionally include side draws to provide for the desired fractionation of the cracker effluent and allowing for recovery of desired fractions for recycle to the selective hydrogenation reaction zone 8. In some embodiments, heavy olefins recycled via flow line 34 may be fed as a reflux (not illustrated) to catalytic distillation reactor system 10, providing both liquid flow to the top of the column and for vaporization of the recycled components prior to feed to cracking reaction zone 22.

Figure 4:
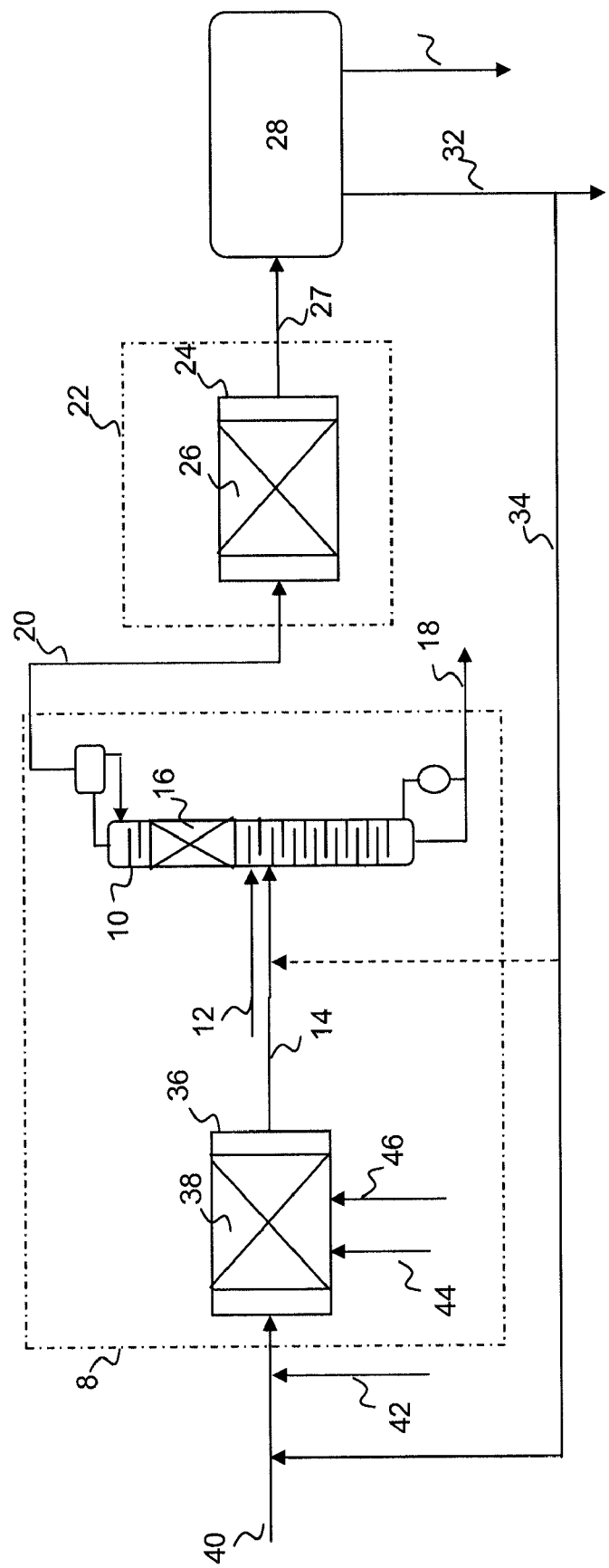
FIG. 4 illustrates a process for the production of olefins according to embodiments disclosed herein.

Referring now to FIG. 4, a process for the production of olefins according to embodiments disclosed herein is illustrated, where like numerals represent like parts. In this embodiment, the selective hydrogenation reaction zone 8 includes one or more fixed bed reactors 36 in series with catalytic distillation reactor system 10 for selectively hydrogenating the diolefins. Fixed bed reactor 36 may include one or more beds 38 of a selective hydrogenation catalyst, where the beds 38 may contain the same or different catalysts. Hydrocarbon feedstock may be fed along with hydrogen via flow lines 40 and 42, respectively, to the inlet of fixed bed reactor 36. As illustrated, hydrogen addition may be staged along the length of the fixed bed reactor 36 via flow lines 44 and 46, for example. The effluent from the fixed bed reactor 36 may be recovered via flow line 14 (hydrocarbon feedstock fed to the catalytic distillation reactor system) and processed as described above.

Also as illustrated in FIG. 4, the heavy olefin recycle may be fed via flow line 34 upstream of either or both the fixed bed reactor 36 and the catalytic distillation reactor system 10. The placement of recycle may depend on the need to control heat release in the various reaction zones, among other factors. For example, where the hydrocarbon feedstock is rich in dienes, such as a butadiene stream or a C5 diolefin stream containing 50% or more dienes, dilution of the hydrocarbon feedstock through the fixed bed reactor system may be desired. This recycle is typically generated by cooling the liquid effluent 14 from the reactor and recycling the partially or totally converted stream back to the reactor entrance.

Figure 5:
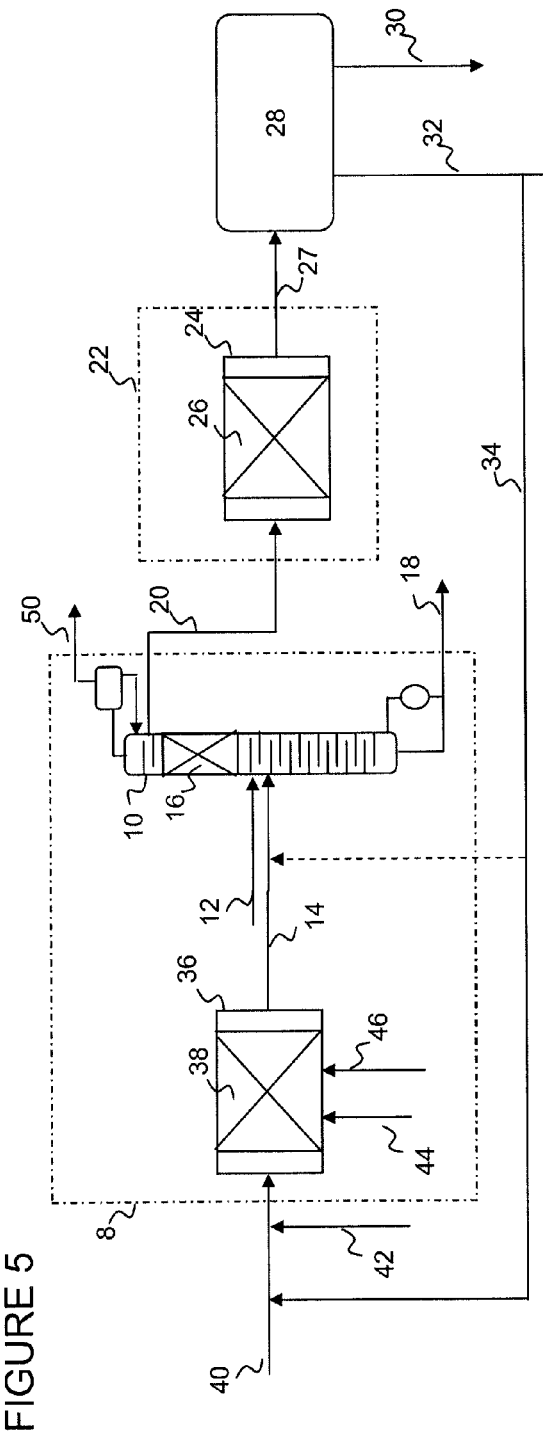
FIG. 5 illustrates a process for the production of olefins according to embodiments disclosed herein.

Referring now to FIG. 5, a process for the production of olefins according to embodiments disclosed herein is illustrated, where like numerals represent like parts. In this embodiment, the selectively hydrogenated olefins fed to the cracking reaction zone 22 may be recovered from catalytic distillation reactor system 10 as a side draw via flow line 20. The side draw may be a vapor phase draw, a liquid phase draw, or a mixed phase draw. In some embodiments, a liquid phase draw may be used to limit the hydrogen concentration in the feed to cracking reaction zone 22. Catalytic distillation reactor system 10 may be operated under a full reflux, and a hydrogen vent may be recovered via flow line 50.

Figure 6:
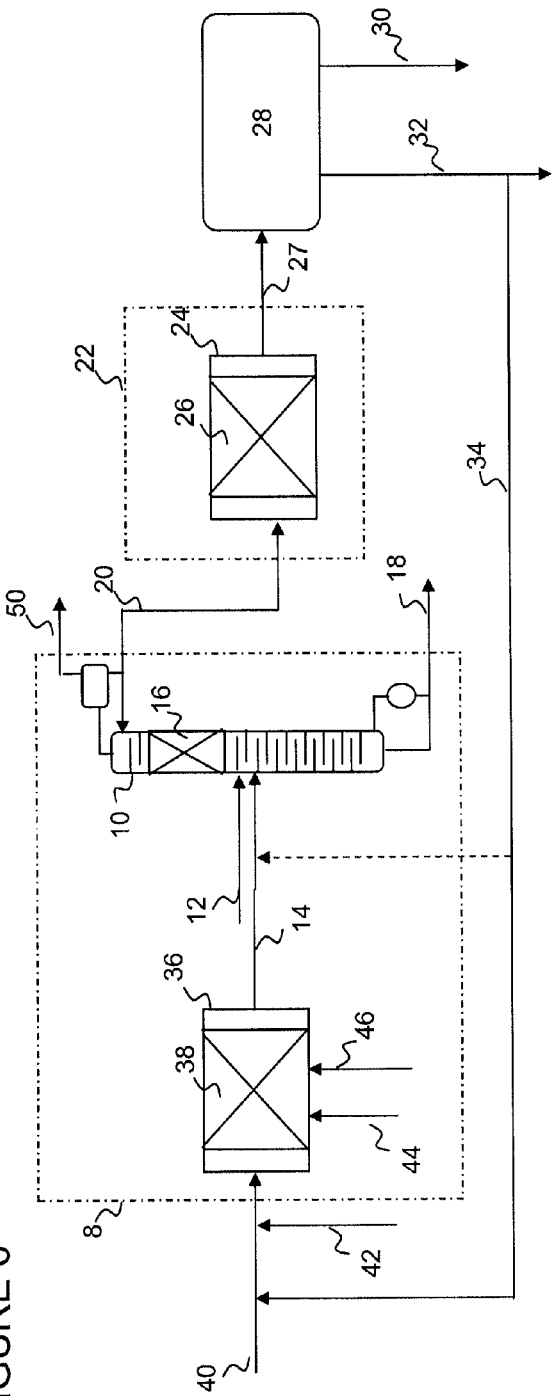
FIG. 6 illustrates a process for the production of olefins according to embodiments disclosed herein.

Referring now to FIG. 6, a process for the production of olefins according to embodiments disclosed herein is illustrated, where like numerals represent like parts. In this embodiment, the selectively hydrogenated olefins fed to the cracking reaction zone 22 may be recovered from catalytic distillation reactor system 10 as an overhead liquid draw via flow line 20, similarly limiting the hydrogen concentration in the feed to cracking reaction zone 22.

Where a liquid phase draw is used in FIGS. 5 and 6, it may be necessary to vaporize the olefin-containing feed using one or more heat exchangers (not shown). While the duty requirements of the embodiments of FIGS. 5 and 6 may be higher than where a vapor phase draw is used, such as for FIGS. 3 and 4 (overhead vapor draw) or for FIG. 5 (vapor phase side draw), it may be necessary to separate the small amount of hydrogen contained in the vapor draw in downstream processes.

As described above, embodiments disclosed herein provide for the production of light olefins from heavier olefins. More specifically, embodiments disclosed herein advantageously provide for an integrated selective hydrogenation of hydrocarbon feedstocks containing dienes. Integration of the selective hydrogenation via recovery of a vapor phase draw may provide for elimination of a pasteurization section, allowing the overhead vapor to go directly to the reaction section without re-vaporization of the hydrocarbon feed to the cracking reaction zone. Selective hydrogenation in a catalytic distillation reactor system may provide for controlled heat release when processing high diene content streams and may additionally reduce overall process equipment piece count.

Embodiments disclosed herein may advantageously provide for operation of reactors in a staggered reaction/regeneration cycle. Operating in a staggered reaction/regeneration cycle may allow for production of a consistent reactor effluent, which may improve downstream fractionation operations and develop a more constant composition of hydrocarbon recycle to the selective hydrogenation reaction zone. Use of multiple reactors for the cracking reaction may provide for reactor L/D ratios that allow for better mixing and space velocities than may be attained in a two-reactor system, which may extend the operating life of catalysts.

Embodiments disclosed herein advantageously provide for an integrated regeneration gas system used for concurrent preheat of the hydrocarbon feed to cracking reactors in a reaction cycle and regeneration of catalyst contained in cracking reactors in a regeneration cycle. Use of regeneration gas for preheat of the hydrocarbon feed may allow for elimination of a fired hydrocarbon feed preheater, reducing capital cost and operating expenses significantly. The integrated regeneration gas system may provide for lower peak loads for nitrogen, air, and heater fuel requirements. Less variation in regeneration flows and process duty may additionally be achieved with a staggered reaction/regeneration cycle using an integrated regeneration gas system.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of light olefins, comprising:
    feeding a hydrocarbon stream comprising C4 to C6 olefins to a cracking reaction zone comprising at least four reactors operated in a staggered reaction/regeneration cycle;
    contacting at least a portion of the C4 to C6 olefins with a catalyst in one or more of the reactors of the cracking reaction zone operating in a reaction cycle to crack at least a portion of the C4 to C6 olefins to form C2 to C3 olefins;
    recovering an effluent from the cracking reaction zone comprising the C2 to C3 olefins and unreacted C4 to C6 olefins;
    separating the effluent from the cracking reaction zone into at least two fractions including one or more fractions comprising at least one of C2 hydrocarbons, C3 hydrocarbons, and a combination thereof, and one or more fractions comprising at least one of C4 hydrocarbons, C5 hydrocarbons, C6 hydrocarbons, and a combination thereof;
    contacting the hydrocarbon stream with a regeneration gas in indirect heat exchange to increase a temperature of the hydrocarbon stream prior to the contacting at least a portion of the C4 to C6 olefins with a catalyst in reactors of the cracking reaction zone in a reaction cycle;
    feeding the regeneration gas and at least one of oxygen and air to one or more of the reactors in the cracking reaction zone operating in a regeneration cycle to regenerate the catalyst contained therein;
    recovering a regeneration gas effluent comprising combustion products from the reactors in the cracking reaction zone in a regeneration cycle;
    withdrawing at least a portion of the recovered regeneration gas effluent comprising combustion products as a purge;
    combining at least a portion of the regeneration gas effluent with make-up nitrogen to form a mixed regeneration gas;
    heating the compressed mixed regeneration gas to a temperature in the range from about 600° C. to about 1000° C.; and
    feeding the heated mixed regeneration gas to the cracking reaction zone as the regeneration gas.

2. The process of claim 1, further comprising controlling a total oxygen content in the regeneration gas and the at least one of oxygen and air fed to the reactors in the regeneration cycle.

3. The process of claim 1, further comprising at least one of:
    contacting the hydrocarbon stream with the effluent from the cracking reaction zone in indirect heat exchange to increase a temperature of the hydrocarbon stream prior to the contacting the hydrocarbon stream with the regeneration gas;
    compressing the mixed regeneration gas; and
    contacting the regeneration gas effluent in indirect heat exchange with the compressed mixed regeneration gas.

4. The process of claim 1, further comprising:
    feeding hydrogen and a C4 to C6 hydrocarbon stream comprising dienes and olefins to a hydrogenation reaction zone comprising a catalytic distillation reactor system containing a selective hydrogenation catalyst;
    concurrently in the catalytic distillation reactor system:
        contacting hydrogen and C4 to C6 dienes with the selective hydrogenation catalyst to selectively hydrogenate C4 to C6 dienes to form additional olefins;
        recovering an effluent from the catalytic distillation reactor system comprising the C4 to C6 olefins and the additional olefins;
    feeding at least a portion of the effluent from the catalytic distillation reactor system to the cracking reaction zone as the hydrocarbon stream comprising C4 to C6 olefins.

5. The process of claim 4, further comprising recycling at least a portion of the one or more fractions comprising C4 hydrocarbons, C5 hydrocarbons, C6 hydrocarbons, and a combination thereof to the hydrogenation reaction zone.

6. The process of claim 4, wherein the hydrogenation reaction zone further comprises a fixed bed reactor upstream of the catalytic distillation reactor system, the process further comprising:
    feeding hydrogen and the C4 to C6 hydrocarbon stream comprising dienes and olefins to the fixed bed reactor containing a second selective hydrogenation catalyst; and
    contacting hydrogen and C4 to C6 dienes with the second selective hydrogenation catalyst to selectively hydrogenate C4 to C6 dienes to form additional olefins.

7. The process of claim 4, wherein the effluent from the catalytic distillation reactor system comprising the C4 to C6 olefins and the additional olefins is recovered from the catalytic distillation reactor system as an overheads fraction.

8. The process of claim 7, wherein the overheads fraction is recovered as a vapor phase.

9. The process of claim 4, wherein the effluent from the catalytic distillation reactor system comprising the C4 to C6 olefins and the additional olefins is recovered from the catalytic distillation reactor system as a side draw.

10. The process of claim 9, wherein the side draw is recovered as a vapor phase, a liquid phase, or a combination thereof.

11. The process of claim 4, wherein the C4 to C6 hydrocarbon stream comprising dienes and olefins comprises a C5 olefin and diolefin stream comprising C5 olefins, C5 dienes, and cyclopentadiene, the process further comprising recovering a hydrocarbon fraction including cyclopentene as a bottoms fraction from the catalytic distillation reactor system.

12. A process for the production of light olefins, comprising:
feeding hydrogen and a C4 to C6 hydrocarbon stream comprising dienes and olefins to a first reaction zone comprising a catalytic distillation reactor system containing a selective hydrogenation catalyst;
concurrently in the catalytic distillation reactor system:
contacting hydrogen and C4 to C6 dienes with the selective hydrogenation catalyst to selectively hydrogenate C4 to C6 dienes to form additional olefins;
recovering an effluent from the catalytic distillation reactor system comprising the C4 to C6 olefins and the additional olefins;
feeding at least a portion of the effluent from the catalytic distillation reactor system to a second reaction zone, wherein the second reaction zone comprises at least four reactors operated in a staggered reaction/regeneration cycle;
contacting at least a portion of the effluent from the catalytic distillation reactor system with a catalyst in one or more reactors of the second reaction zone operating in a reaction cycle to crack at least a portion of the C4 to C6 olefins to form C2 to C3 olefins;
recovering an effluent from the second reaction zone comprising the C2 to C3 olefins and unreacted C4 to C6 olefins;
separating the effluent from the second reaction zone into at least two fractions including one or more fractions comprising at least one of C2 hydrocarbons, C3 hydrocarbons, and a combination thereof, and one or more fractions comprising at least one of C4 hydrocarbons, C5 hydrocarbons, C6 hydrocarbons, and a combination thereof;
recycling at least a portion of the one or more fractions comprising C4 hydrocarbons, C5 hydrocarbons, C6 hydrocarbons, and a combination thereof to the first reaction zone;
contacting the effluent from the catalytic distillation reaction system with a regeneration gas in indirect heat exchange to increase a temperature of the effluent prior to the contacting at least a portion of the effluent from the catalytic distillation reactor system with a catalyst in one or more reactors of the second reaction zone operating in a reaction cycle; and
feeding the regeneration gas and at least one of oxygen and air to one or more reactors in the second reaction zone operating in a regeneration cycle to regenerate the catalyst contained therein;
contacting the effluent from the catalytic distillation reaction system with the effluent from the reactors operating in the reaction cycle in the second reaction zone in indirect heat exchange to increase a temperature of the effluent from the catalytic distillation reaction system prior to the contacting the effluent from the catalytic distillation reaction system with the regeneration gas;
recovering a regeneration gas effluent comprising combustion products from the reactors in the second reaction zone in a regeneration cycle;
withdrawing at least a portion of the recovered regeneration gas effluent comprising combustion products as a purge;
combining at least a portion of the regeneration gas effluent with make-up nitrogen to form a mixed regeneration gas;
compressing the mixed regeneration gas;
contacting the regeneration gas effluent in indirect heat exchange with the compressed mixed regeneration gas;
heating the compressed mixed regeneration gas to a temperature in the range from about 600° C. to about 1000° C.; and
feeding the heated mixed regeneration gas to the second reaction zone as the regeneration gas.

13. The process of claim 12, wherein the first reaction zone further comprises a fixed bed reactor upstream of the catalytic distillation reactor system, the process further comprising:
feeding hydrogen and the C4 to C6 hydrocarbon stream comprising dienes and olefins to the fixed bed reactor containing a second selective hydrogenation catalyst; and
contacting hydrogen and C4 to C6 dienes with the second selective hydrogenation catalyst to selectively hydrogenate C4 to C6 dienes to form additional olefins.

14. The process of claim 12, wherein the effluent from the catalytic distillation reactor system comprising the C4 to C6 olefins and the additional olefins is recovered from the catalytic distillation reactor system as an overheads fraction.

15. The process of claim 14, wherein the overheads fraction is recovered as a vapor phase.

16. The process of claim 12, wherein the effluent from the catalytic distillation reactor system comprising the C4 to C6 olefins and the additional olefins is recovered from the catalytic distillation reactor system as a side draw.

17. The process of claim 16, wherein the side draw is recovered as a vapor phase, a liquid phase, or a combination thereof.

18. The process of claim 12, wherein the C4 to C6 hydrocarbon stream comprising dienes and olefins comprises a C5 olefin and diolefin stream comprising C5 olefins, C5 dienes, and cyclopentadiene, the process further comprising recovering a hydrocarbon fraction including cyclopentadiene as a bottoms fraction from the catalytic distillation reactor system.

19. A process for the production of light olefins, comprising:
feeding hydrogen and a C5 hydrocarbon stream comprising C5 dienes, C5 olefins and cyclopentadiene to a first reaction zone comprising a catalytic distillation reactor system containing a selective hydrogenation catalyst;
concurrently in the catalytic distillation reactor system:
contacting hydrogen and C5 dienes with the selective hydrogenation catalyst to selectively hydrogenate C5 dienes to form additional olefins and hydrogenate at least a portion of the cyclopentadiene to cyclopentene;

recovering an effluent from the catalytic distillation reactor system comprising the C5 olefins and the additional olefins;

recovering a bottoms fraction from the catalytic distillation reactor system comprising cyclopentene;

feeding at least a portion of the effluent from the catalytic distillation reactor system to a second reaction zone, wherein the second reaction zone comprises at least four reactors operated in a staggered reaction/regeneration cycle;

contacting at least a portion of the effluent from the catalytic distillation reactor system with a catalyst in one or more reactors of the second reaction zone operating in a reaction cycle to crack at least a portion of the C5 olefins to form C2 to C3 olefins;

recovering an effluent from the second reaction zone comprising the C2 to C3 olefins and unreacted C5 olefins;

separating the effluent from the second reaction zone into at least two fractions including one or more fractions comprising at least one of C2 hydrocarbons, C3 hydrocarbons, and a combination thereof, and a fraction comprising C5 hydrocarbons;

recycling at least a portion of the fraction comprising C5 hydrocarbons to the first reaction zone;

contacting the effluent from the catalytic distillation reaction system with a regeneration gas in indirect heat exchange to increase a temperature of the effluent prior to the contacting at least a portion of the effluent from the catalytic distillation reactor system with a catalyst in one or more reactors of the second reaction zone operating in a reaction cycle; and feeding the regeneration gas and at least one of oxygen and air to one or more reactors in the second reaction zone operating in a regeneration cycle to regenerate the catalyst contained therein;

contacting the effluent from the catalytic distillation reaction system with the effluent from the second reaction zone in indirect heat exchange to increase a temperature of the effluent from the catalytic distillation reaction system prior to the contacting the effluent from the catalytic distillation reaction system with the regeneration gas;

recovering a regeneration gas effluent comprising combustion products from the reactors in the second reaction zone in a regeneration cycle;

withdrawing at least a portion of the recovered regeneration gas effluent comprising combustion products as a purge;

combining at least a portion of the regeneration gas effluent with make-up nitrogen to form a mixed regeneration gas;

compressing the mixed regeneration gas;

contacting the regeneration gas effluent with the compressed mixed regeneration gas;

heating the compressed mixed regeneration gas to a temperature in the range from about 600° C. to about 1000° C.; and feeding the heated mixed regeneration gas to the second reaction zone as the regeneration gas.

20. The process of claim 19, wherein the first reaction zone further comprises a fixed bed reactor upstream of the catalytic distillation reactor system, the process further comprising:

feeding hydrogen and the C5 hydrocarbon stream to the fixed bed reactor containing a second selective hydrogenation catalyst; and contacting hydrogen and C5 dienes with the second selective hydrogenation catalyst to selectively hydrogenate C5 dienes to form additional olefins.

21. The process of claim 19, wherein the effluent from the catalytic distillation reactor system comprising the C5 olefins and the additional olefins is recovered from the catalytic distillation reactor system as an overheads fraction.

22. The process of claim 21, wherein the overheads fraction is recovered as a vapor phase.

23. The process of claim 19, wherein the effluent from the catalytic distillation reactor system comprising the C5 olefins and the additional olefins is recovered from the catalytic distillation reactor system as a side draw.

24. The process of claim 23, wherein the side draw is recovered as a vapor phase, a liquid phase, or a combination thereof.

* * * * *